(12) United States Patent
Sugie et al.

(10) Patent No.: US 10,917,572 B2
(45) Date of Patent: Feb. 9, 2021

(54) IMAGE PROCESSING APPARATUS, IMAGE PROCESSING METHOD, AND OPTICAL MEMBER

(71) Applicant: SONY CORPORATION, Tokyo (JP)

(72) Inventors: Yuki Sugie, Kanagawa (JP); Koji Kashima, Kanagawa (JP); Masaya Takemoto, Kanagawa (JP); Kenji Ikeda, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/465,827

(22) PCT Filed: Dec. 5, 2017

(86) PCT No.: PCT/JP2017/043593
§ 371 (c)(1),
(2) Date: May 31, 2019

(87) PCT Pub. No.: WO2018/105592
PCT Pub. Date: Jun. 14, 2018

(65) Prior Publication Data
US 2019/0335104 A1 Oct. 31, 2019

(30) Foreign Application Priority Data

Dec. 9, 2016 (JP) .................................. 2016-239639

(51) Int. Cl.
*H04N 5/232* (2006.01)
*A61B 90/00* (2016.01)
*A61B 1/00* (2006.01)
*A61B 1/06* (2006.01)
*H04N 5/225* (2006.01)

(52) U.S. Cl.
CPC ..... *H04N 5/23267* (2013.01); *A61B 1/00009* (2013.01); *A61B 1/00045* (2013.01); *A61B 1/00096* (2013.01); *A61B 1/0623* (2013.01); *A61B 90/39* (2016.02); *A61B 2090/3945* (2016.02); *H04N 2005/2255* (2013.01)

(58) Field of Classification Search
CPC ... A61B 1/00048; A61B 1/0005; A61B 1/313; A61B 1/00193; A61B 1/0051; A61B 1/00039; A61B 1/00009; G02B 23/2484
See application file for complete search history.

(56) References Cited

U.S. PATENT DOCUMENTS 6,449,103 B1 * 9/2002 Charles .................. G02B 13/06
359/366

* cited by examiner

*Primary Examiner* — James M Pontius
(74) *Attorney, Agent, or Firm* — Xsensus LLP

(57) ABSTRACT

An endoscopic system including an endoscope including an optical element including a marker disposed thereon, an optical formation device that changes an angle of view, and an image capturing device receiving light from the optical element via the optical formation device and processing circuitry that identifies the angle of view from an image captured by the image capturing device based on the marker in the image.

27 Claims, 14 Drawing Sheets

[Fig. 1]
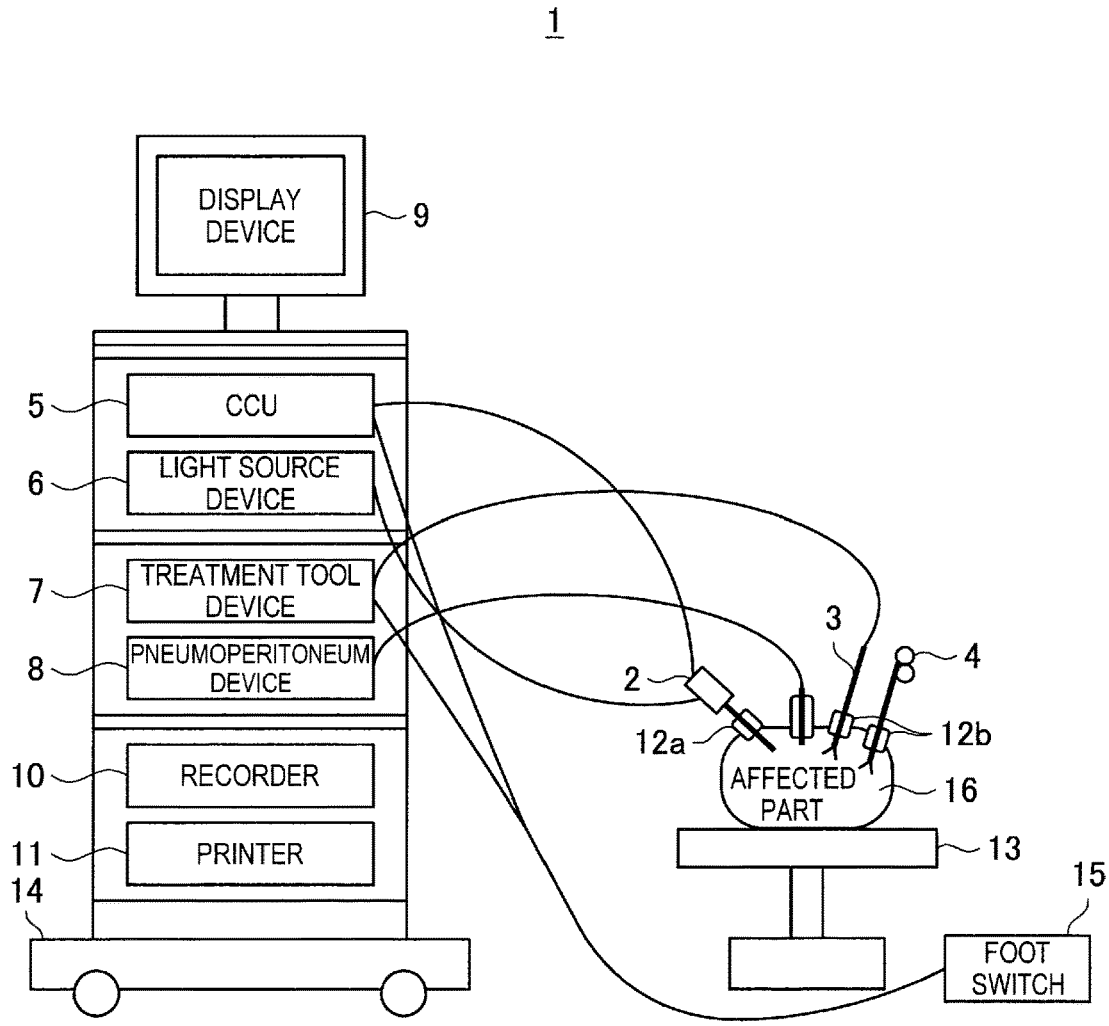
[Fig. 2]
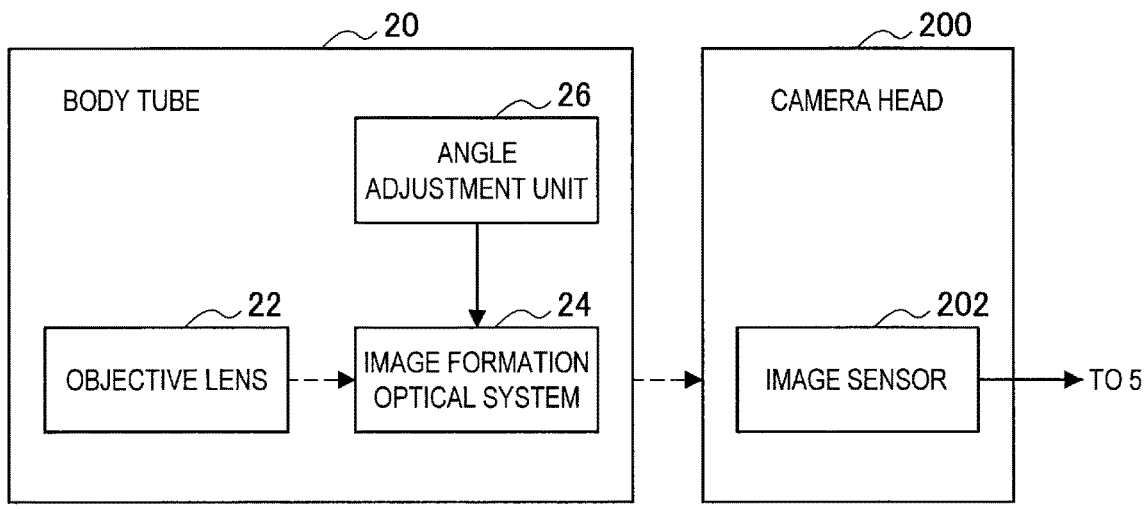

[Fig. 3]
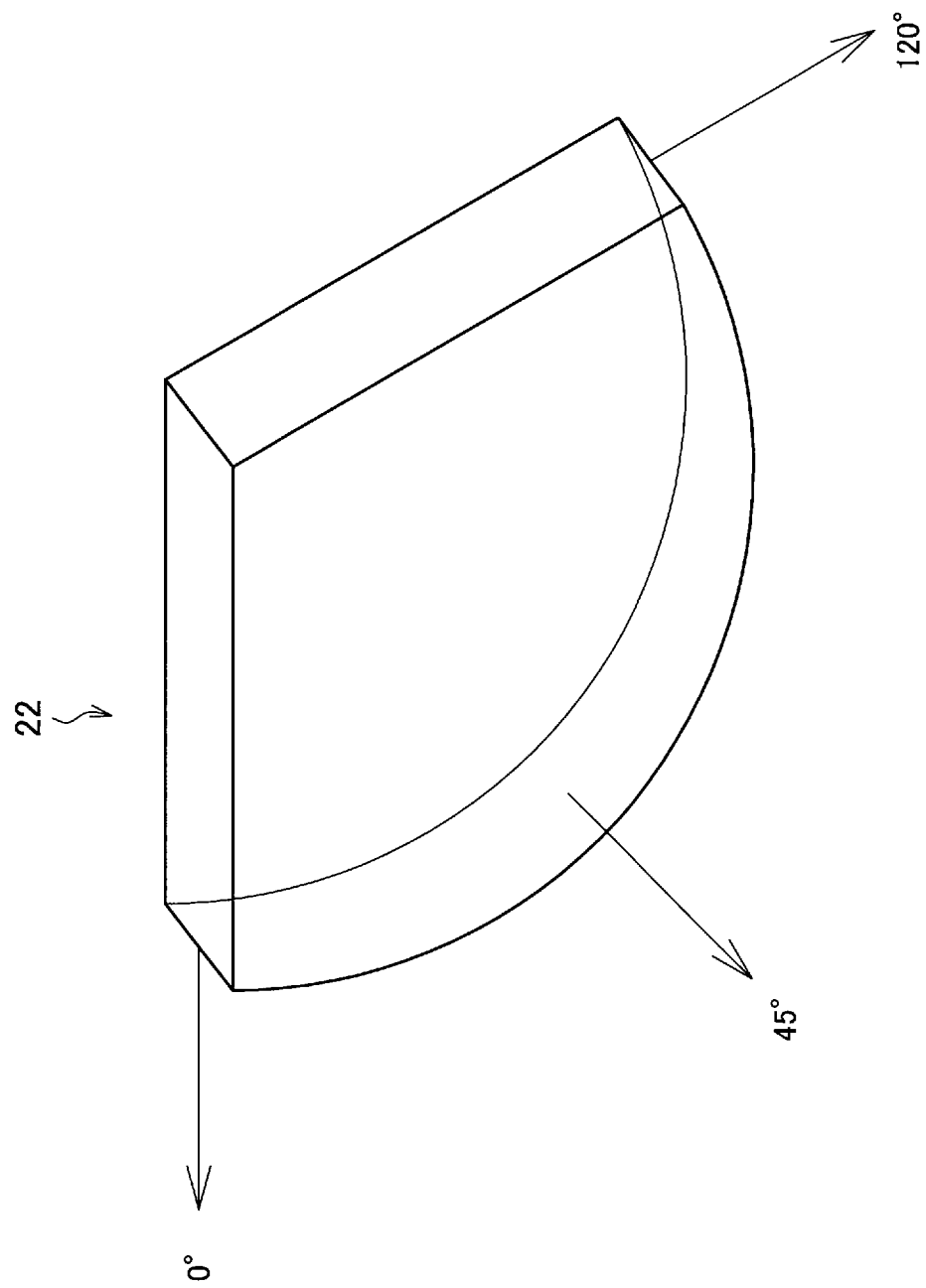

[Fig. 4]
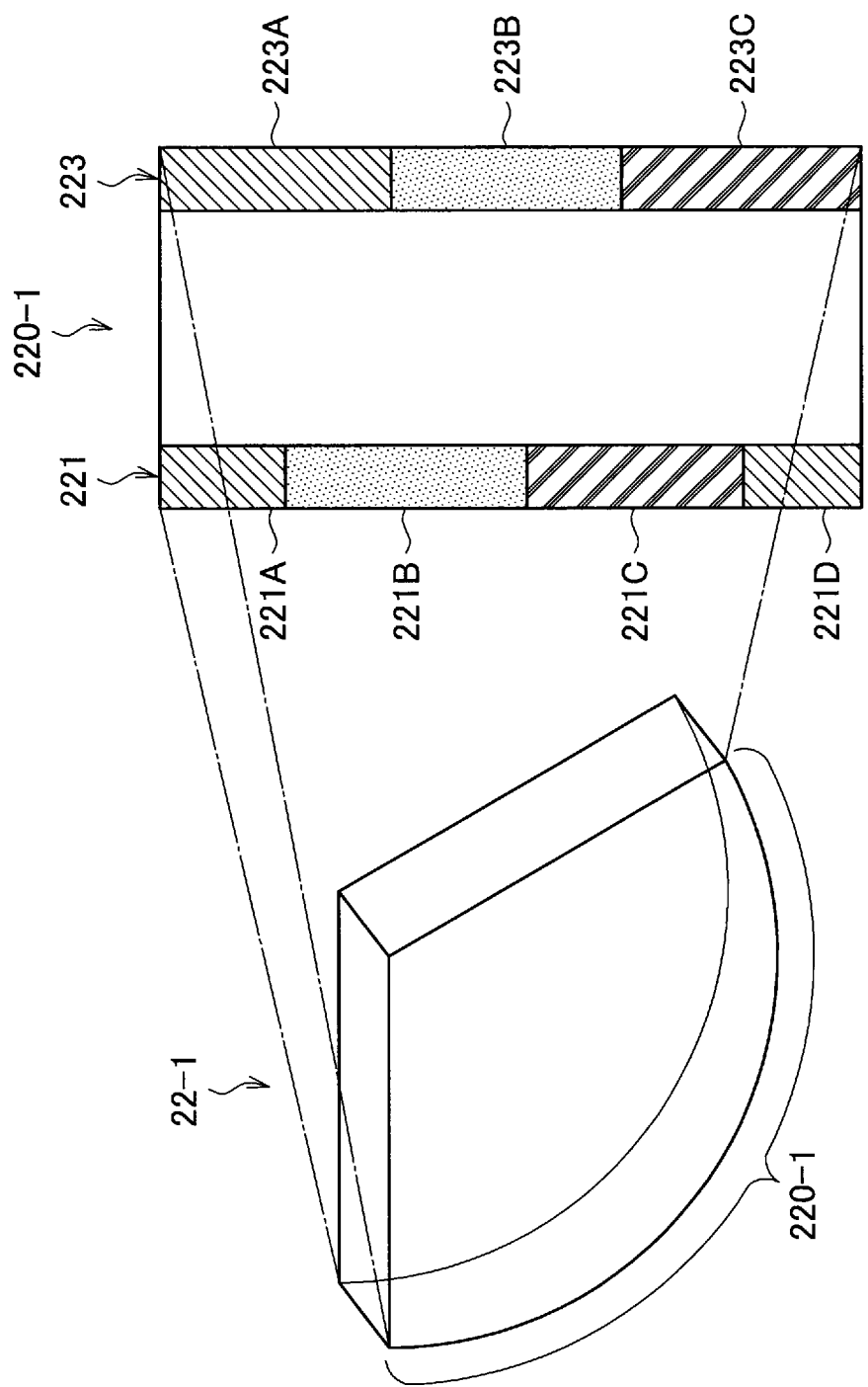

[Fig. 5]
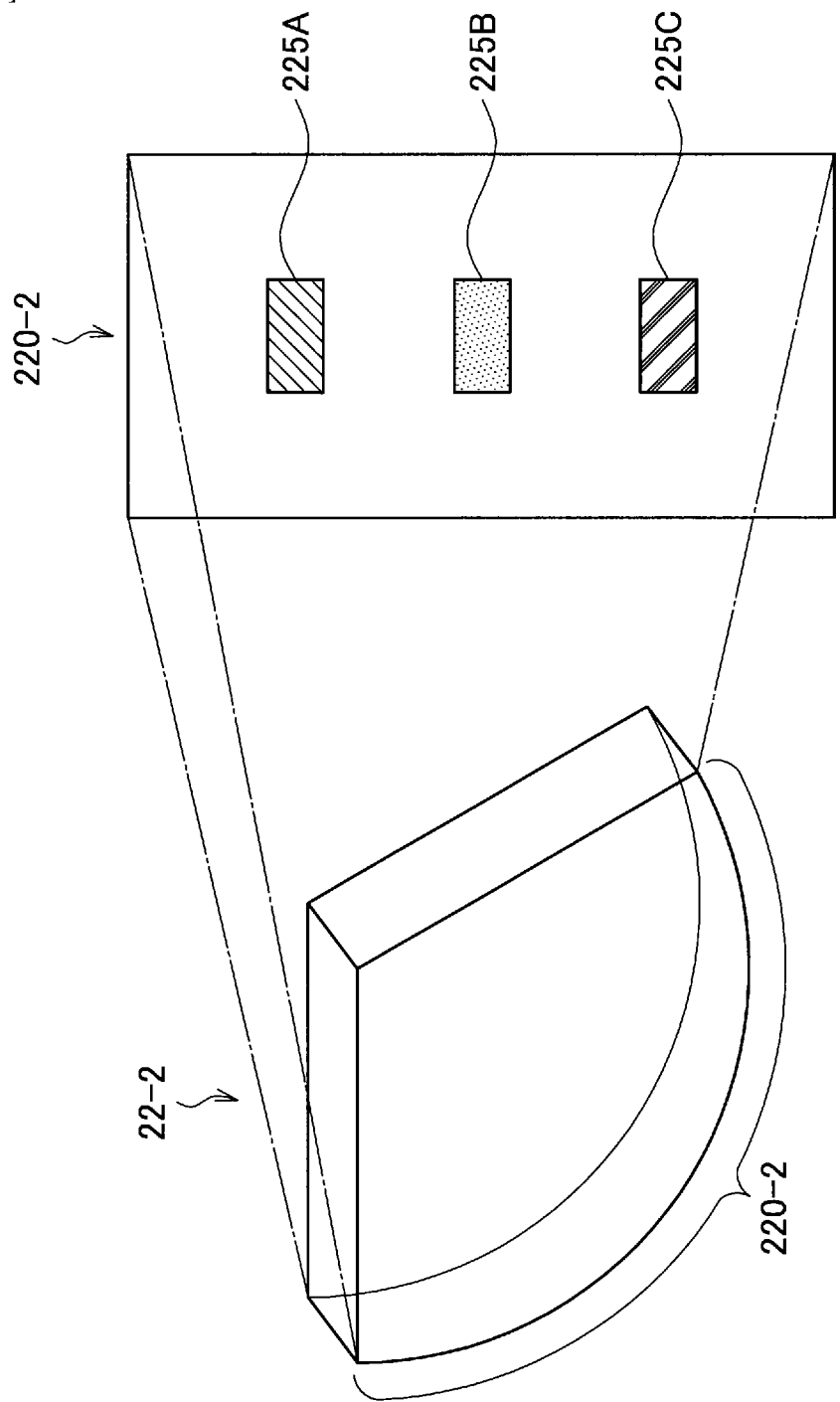

[Fig. 6]
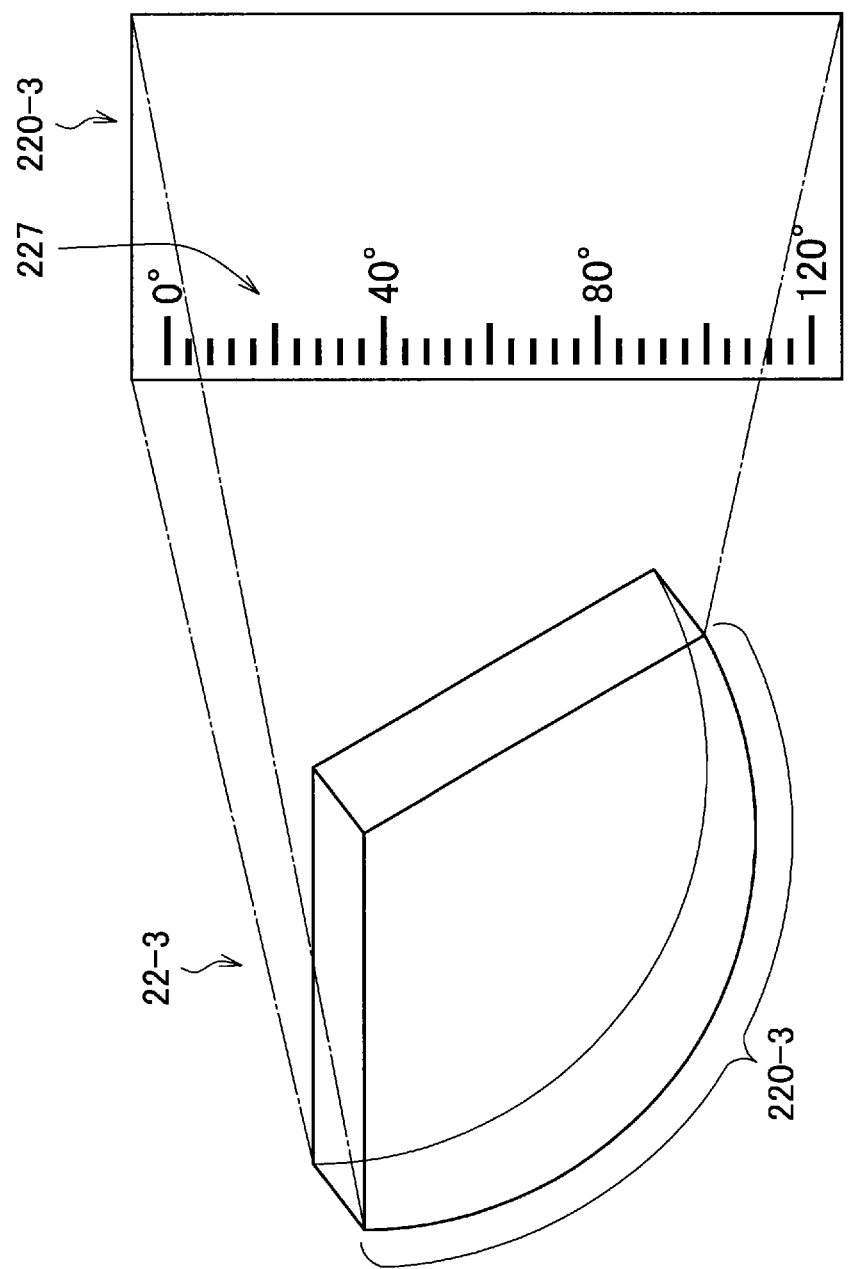

[Fig. 7]
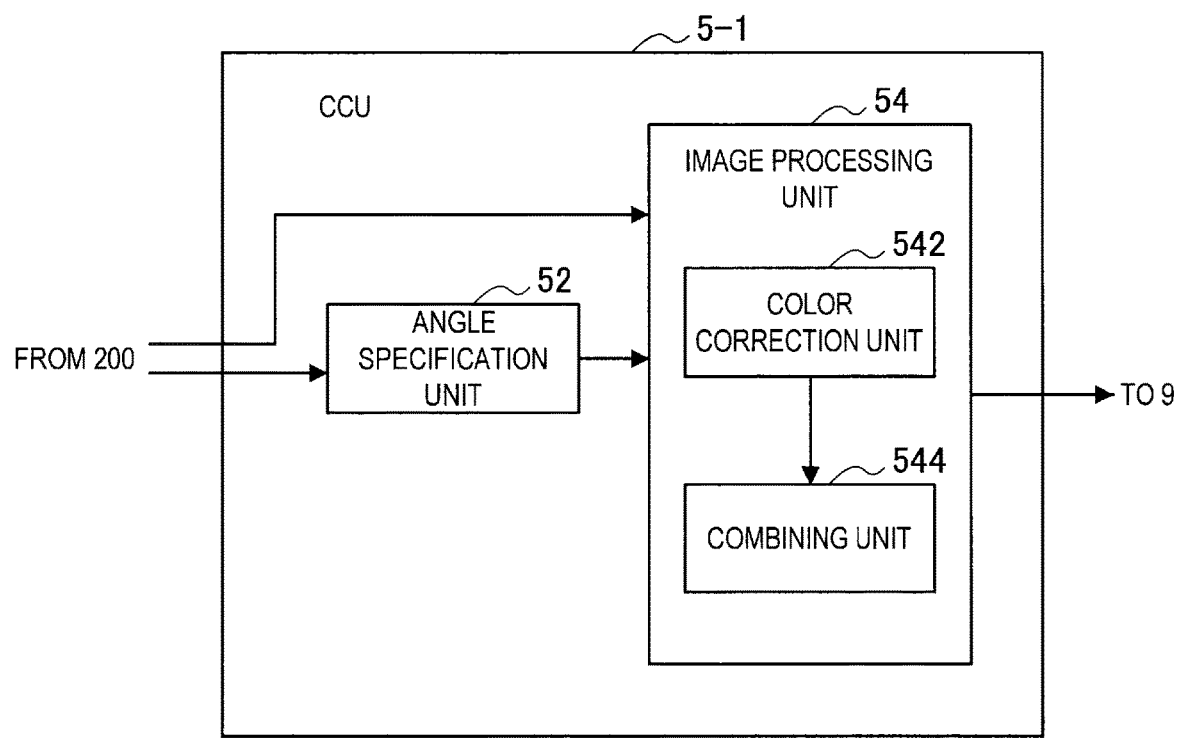

[Fig. 8]
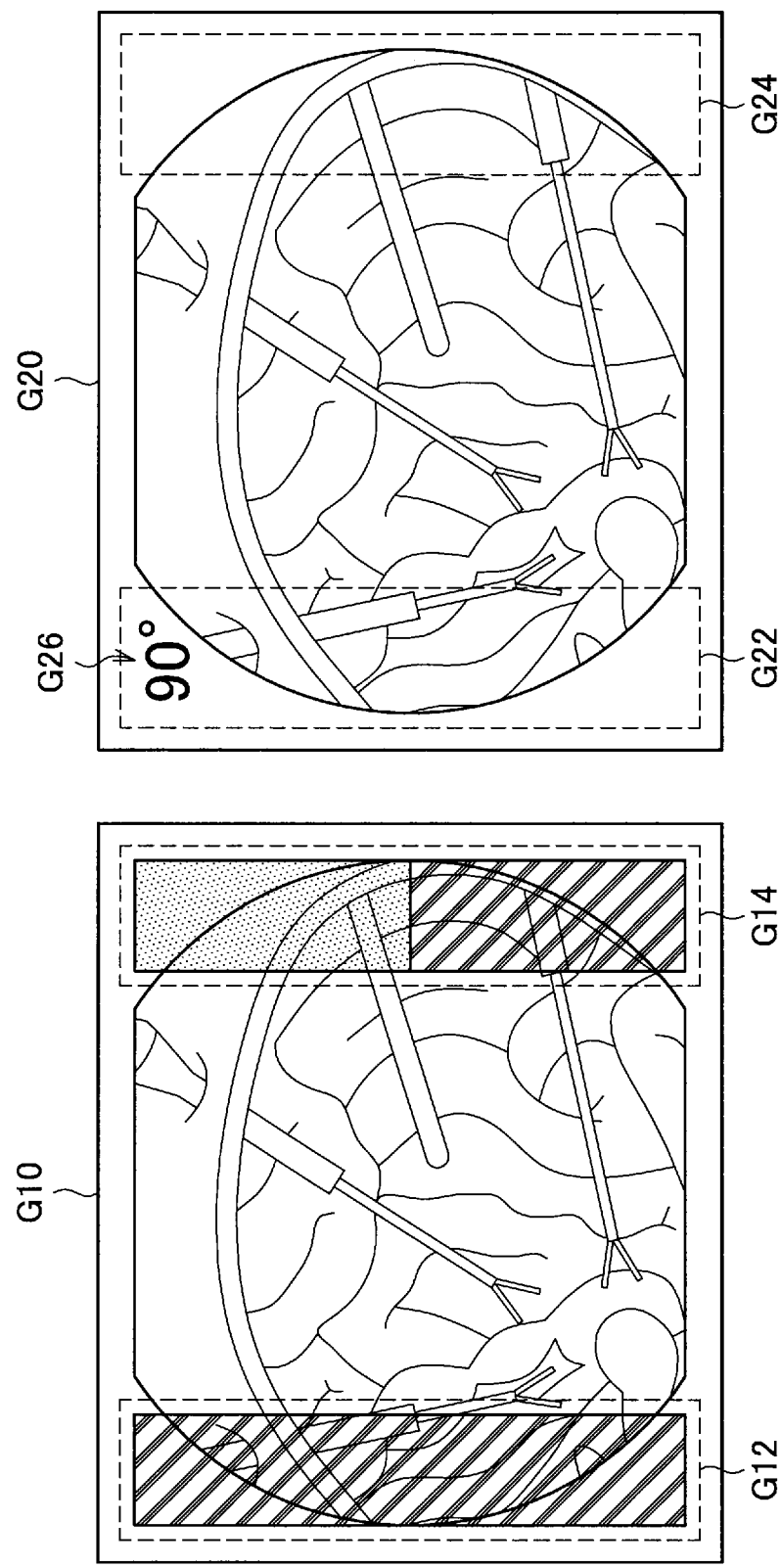

[Fig. 9]
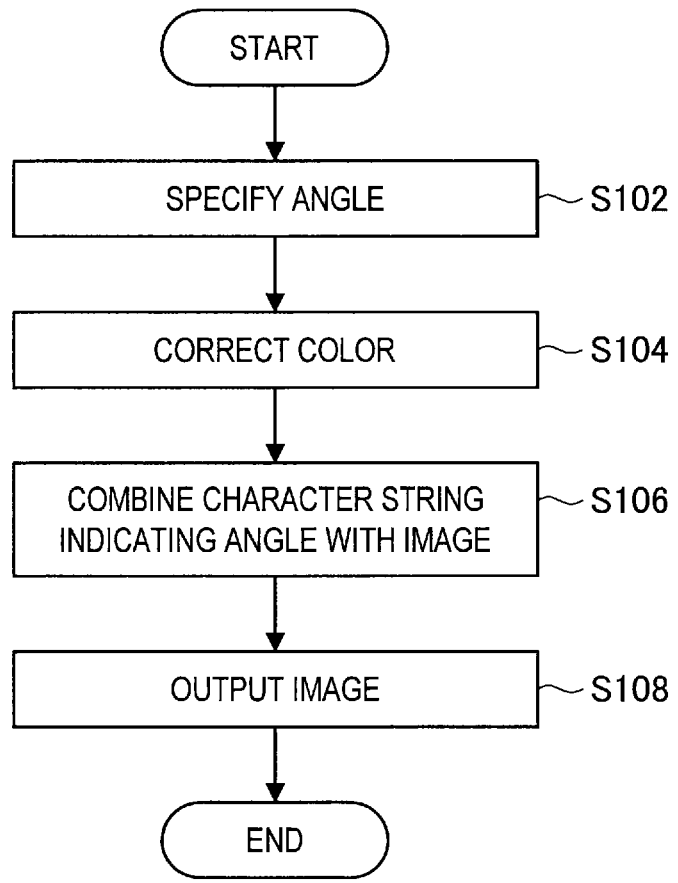

[Fig. 10]
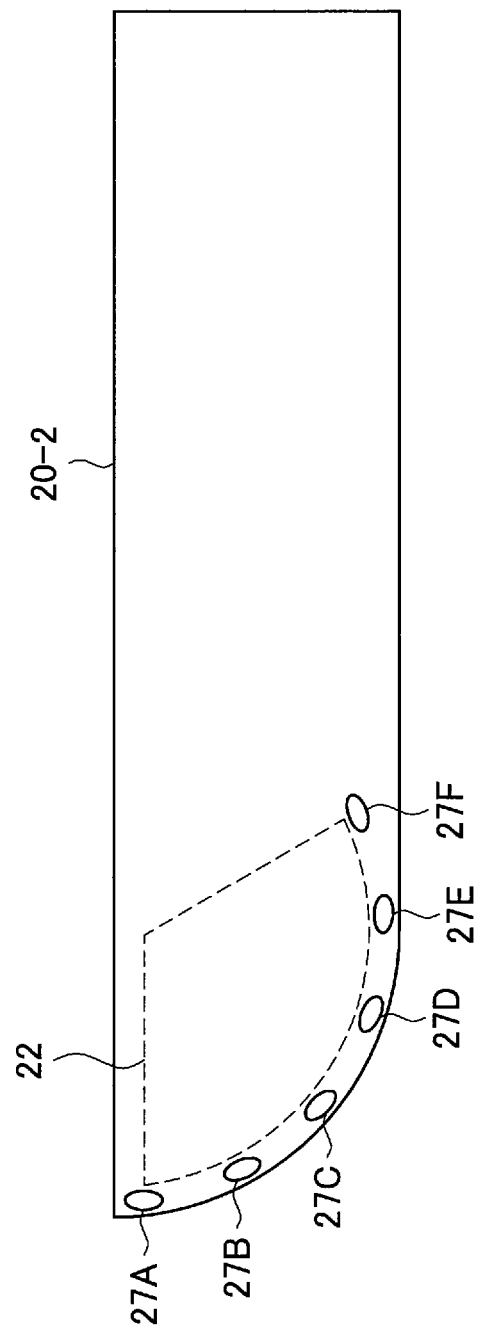

[Fig. 11]
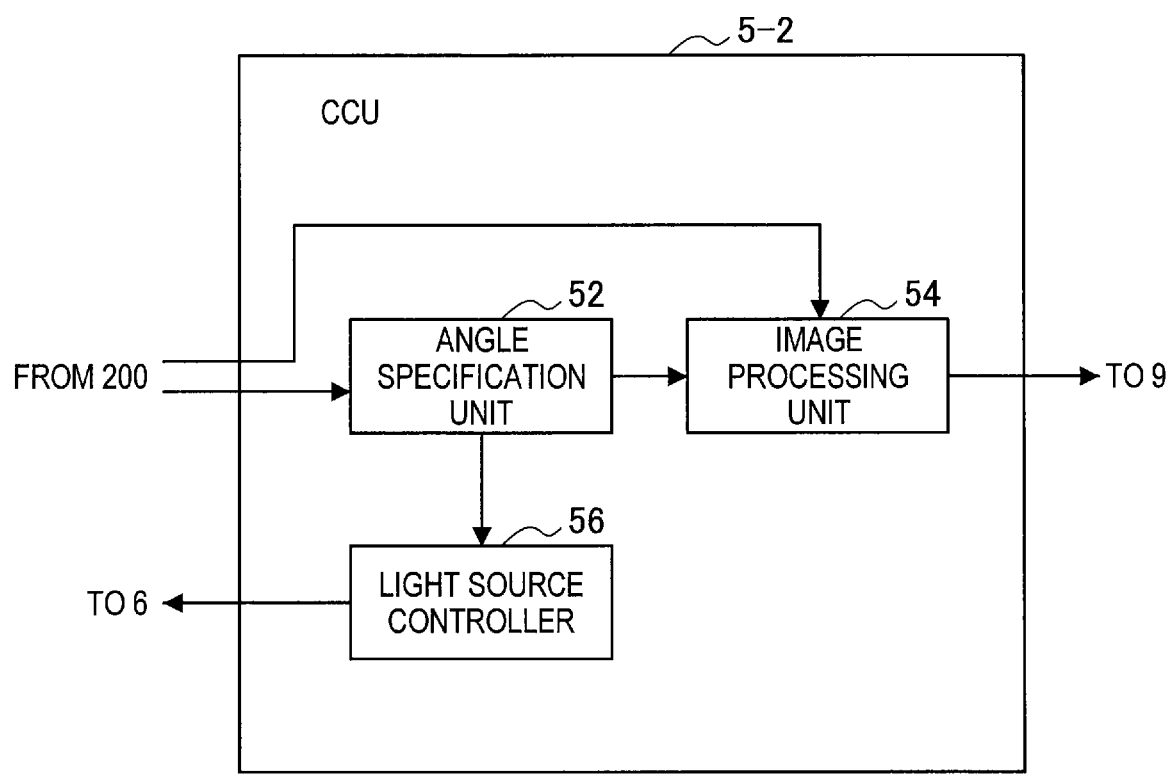

[Fig. 12]
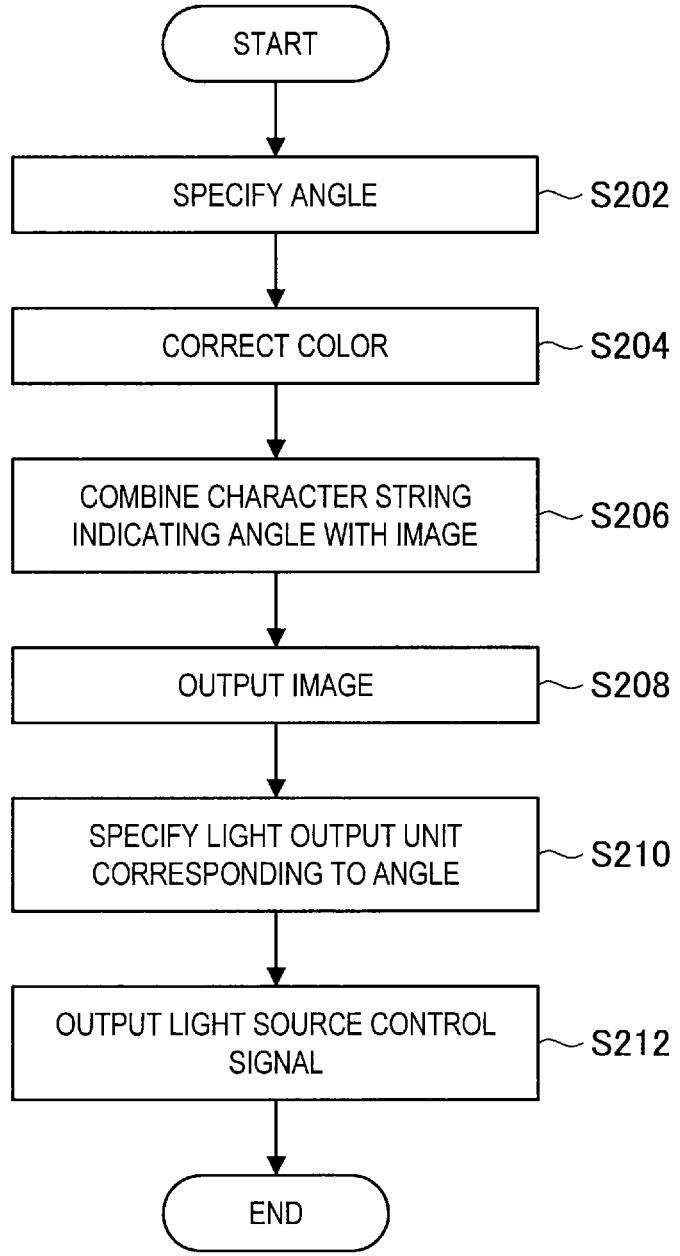

[Fig. 13]
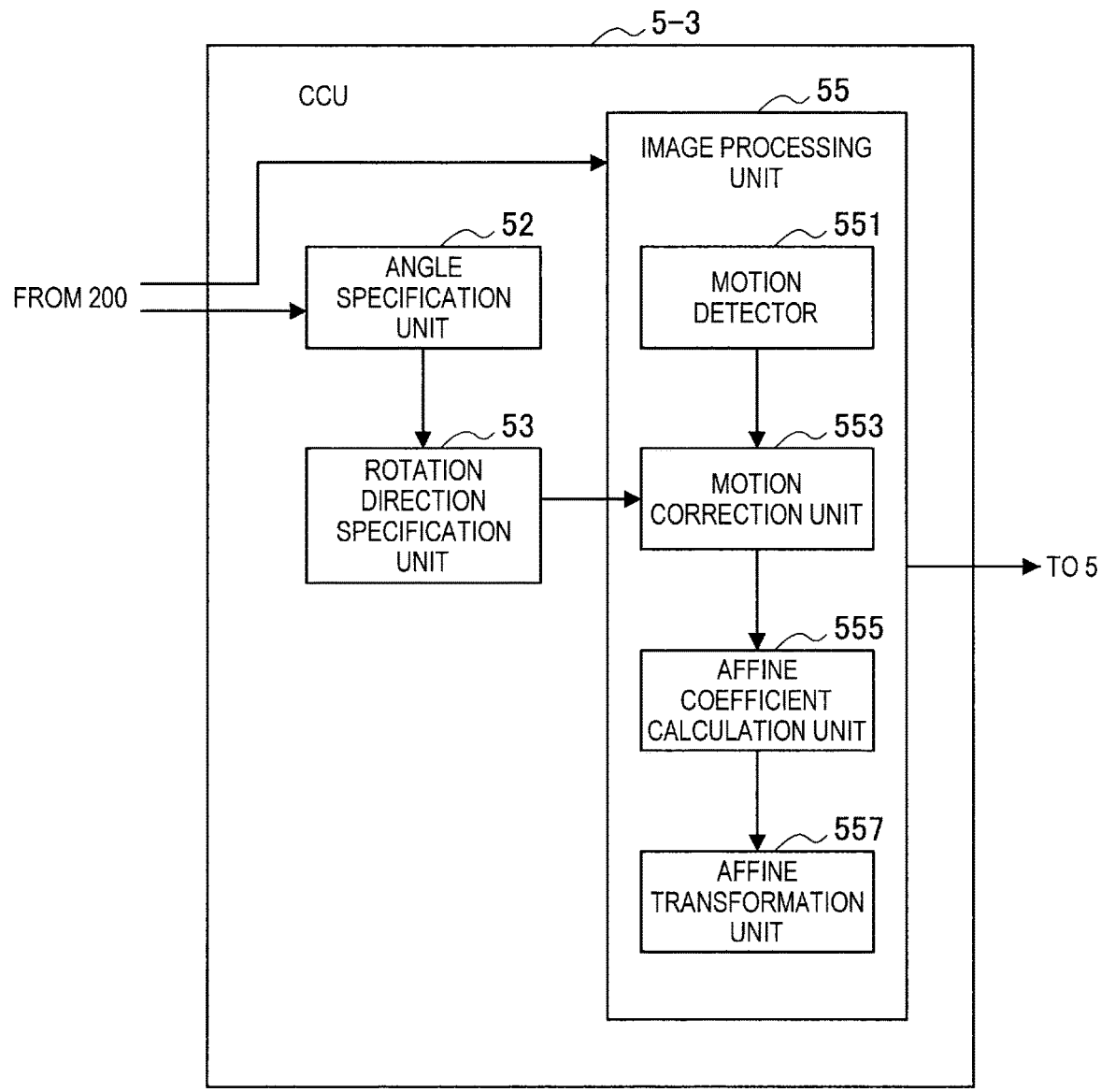

[Fig. 14]
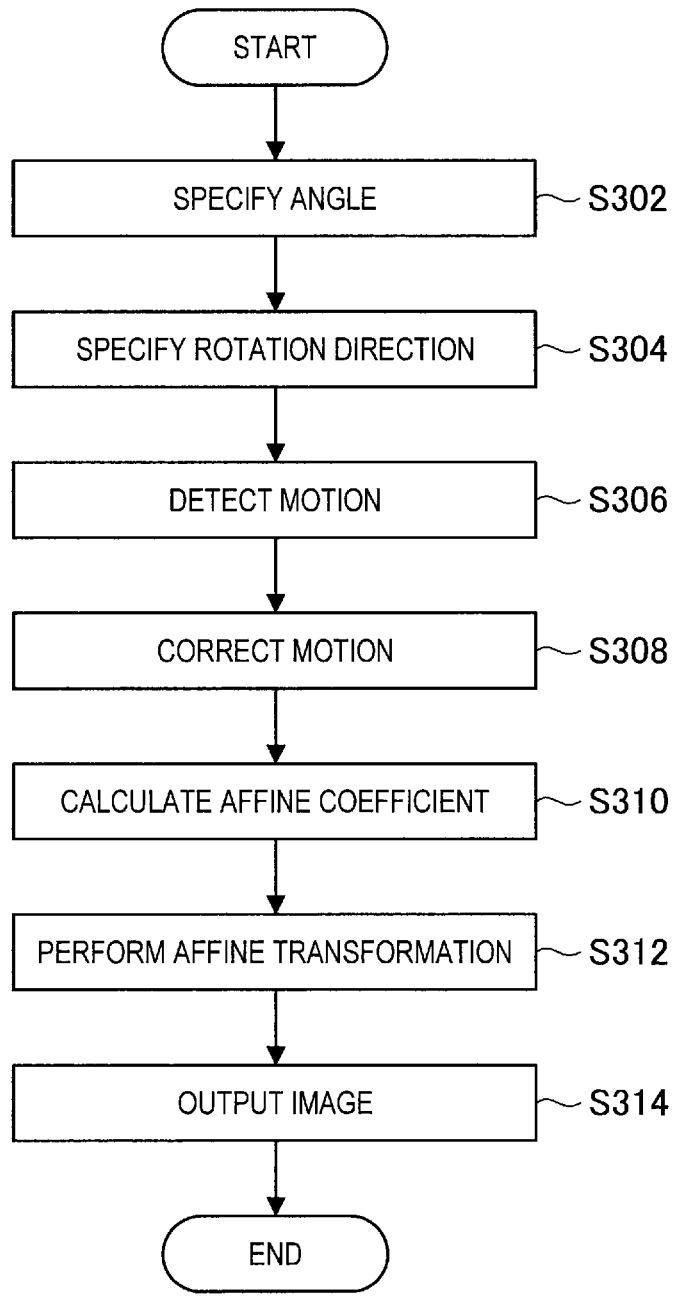

[Fig. 15]
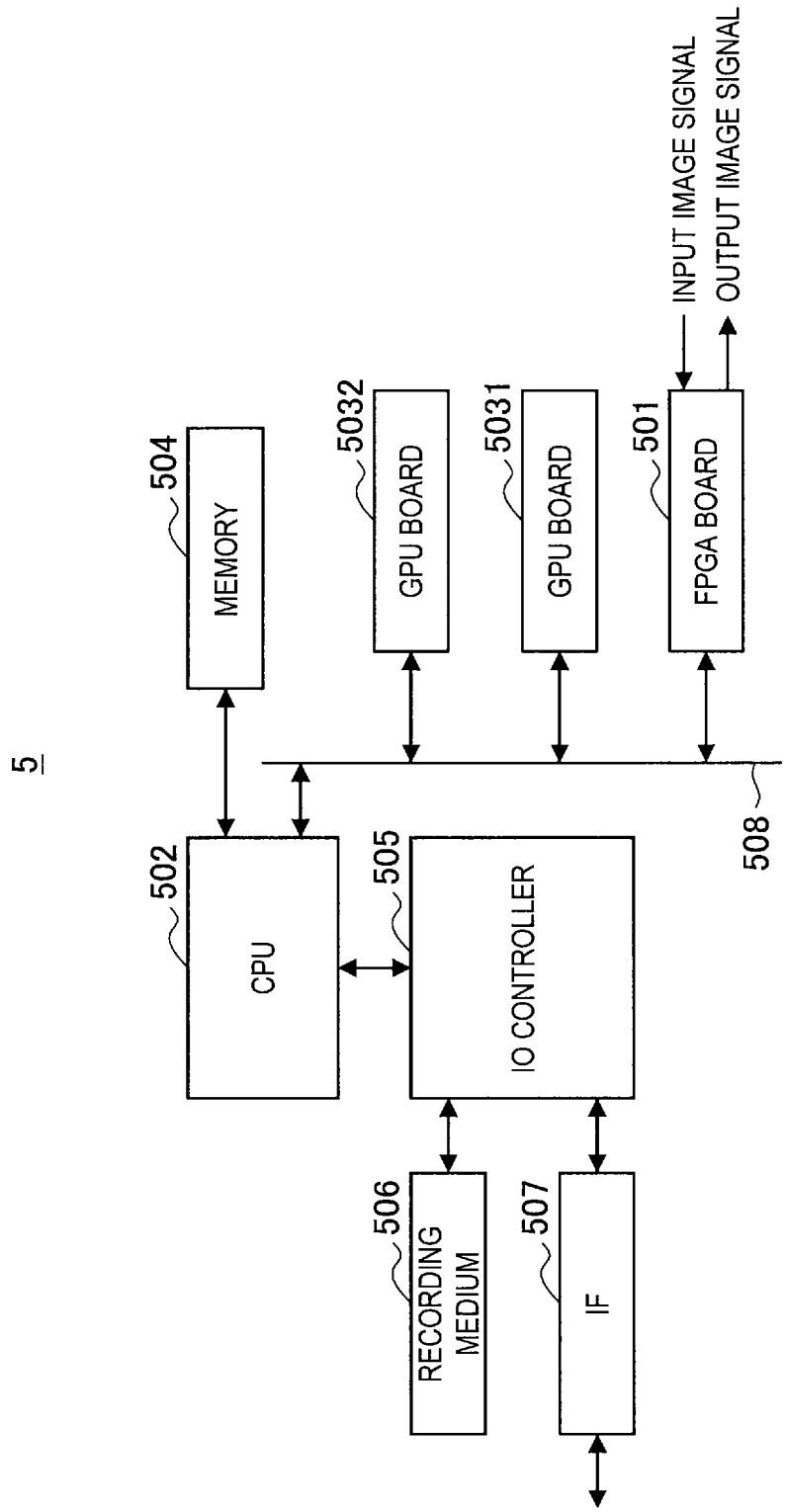

IMAGE PROCESSING APPARATUS, IMAGE PROCESSING METHOD, AND OPTICAL MEMBER

CROSS REFERENCE TO RELATED APPLICATIONS

This application claims the benefit of Japanese Priority Patent Application JP 2016-239639 filed Dec. 9, 2016, the entire contents of which are incorporated herein by reference.

TECHNICAL FIELD

The present disclosure relates to an image processing apparatus, an image processing method, and an optical member.

BACKGROUND ART

In a health care site, endoscopic surgeries using endoscopes have recently been conducted. In an endoscopic surgery, a worker can conduct an examination or a surgery while observing an image which is captured by an endoscope inserted into an observation target (patient) and which is displayed on a monitor.

For example, the following Patent Literature 1 discloses a technology for displaying an endoscopic image by making the vertical and horizontal directions of the endoscopic image captured by an endoscope including an acceleration sensor that detects a rotation angle correspond to the vertical and horizontal manipulation directions of the worker.

Further, since places in which organs are convoluted are observed, the endoscope capable of changing an angle of a line-of-sight direction has been used. With such an endoscope capable of changing the angle of the line-of-sight direction, it becomes possible to save the effort of exchanging endoscopes having different line-of-sight directions.

CITATION LIST

Patent Literature

PTL 1: JP 2006-218027A

SUMMARY

Technical Problem

In the case where the above-mentioned endoscope capable of changing the angle of the line-of-sight direction is used, there has been a case where it is difficult to grasp an angle of a current line-of-sight direction from an image which is captured by the endoscope and displayed on a monitor. In the case where the angle of line-of-sight direction is unclear, it becomes difficult to manipulate the endoscope, and there is a risk that the organs such as the abdominal wall may be wounded.

Accordingly, the present disclosure suggests an image processing apparatus, an image processing method, and an optical member, which are novel and improved, and which can grasp the angle of the line-of-sight direction more easily.

Solution to Problem

According to one embodiment of the present disclosure there is described an endoscopic system including an endoscope including an optical element including a marker disposed thereon, an optical formation device configured to change an angle of view, and an image capturing device receiving light from the optical element via the optical formation device and processing circuitry configured to identify the angle of view from an image captured by the image capturing device based on the marker in the image.

According to another embodiment of the present disclosure there is described a medical image processing device, including processing circuitry configured to identify an angle of view from an image based on a marker in the image, wherein the image is generated from light through the marker on an optical element, and wherein the angle of view is changed relative to the marker in an endoscope imaging device.

According to another embodiment of the present disclosure there is described a medical image processing method including identifying, via processing circuitry, an angle of view from an image based on a marker in the image, wherein the image is generated from light through the marker on an optical element, and wherein the angle of view is changed relative to the marker in an endoscope imaging device including the marker and the optical element.

According to another embodiment of the present disclosure there is described an endoscope including an optical element including a marker disposed thereon, and an optical formation device configured to change an angle of view relative to the marker on the optical element.

Advantageous Effects of Invention

According to the present disclosure described above, the angle of the line-of-sight direction (i.e. angle of view) can be grasped more easily.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 is an explanatory diagram showing an overall configuration of an endoscopic surgery system 1 according to an embodiment of the present disclosure.

FIG. 2 is a block diagram showing an example of a functional configuration of an endoscope 2 according to the embodiment.

FIG. 3 is an explanatory diagram illustrating an objective lens 22 according to the embodiment.

FIG. 4 is an explanatory diagram illustrating an example of a marker included in the objective lens 22 according to the embodiment.

FIG. 5 is an explanatory diagram illustrating another example of a marker included in the objective lens 22 according to the embodiment.

FIG. 6 is an explanatory diagram illustrating another example of a marker included in the objective lens 22 according to the embodiment.

FIG. 7 is a block diagram showing an example of a functional configuration of a CCU 5-1 according to the embodiment.

FIG. 8 is an explanatory diagram showing an example of a captured image and an output image according to the embodiment.

FIG. 9 is a flowchart showing an operation example according to the embodiment.

FIG. 10 is an explanatory diagram illustrating an overview of Modified Example 1.

FIG. 11 is a block diagram showing an example of a functional configuration of a CCU 5-2 according to the modified example.

FIG. 12 is a flowchart showing an operation example of the modified example.

FIG. 13 is a block diagram showing an example of a functional configuration of a CCU 5-3 according to Modified Example 2.

FIG. 14 is a flowchart showing an operation example of the modified example.

FIG. 15 is an explanatory diagram showing a hardware configuration example.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that, in this description and the drawings, structural elements that have substantially the same function and structure are sometimes distinguished from each other using different alphabets after the same reference sign. However, when there is no need in particular to distinguish structural elements that have substantially the same function and structure, the same reference sign alone is attached.

Note that the description will be given in the following order.

<<1. Overview>>
<1-1. Schematic configuration of endoscopic surgery system>
<1-2. Background>
<<2. Configuration>>
<2-1. Configuration of endoscope>
<2-2. Configuration of CCU>
<<3. Operation>>
<<4. Modified Examples>>
<4-1. Modified Example 1>
<4-2. Modified Example 2>
<4-3. Modified Example 3>
<<5. Hardware configuration example>>
<<6. Conclusion>>

1. Overview

1-1. Schematic Configuration of Endoscopic Surgery System

First, with reference to a figure, a schematic configuration (overview) of an endoscopic surgery system according to an embodiment of the present disclosure is described. FIG. 1 is an explanatory diagram showing an overall configuration of an endoscopic surgery system 1 according to an embodiment of the present disclosure. Note that, in the description below, "user" represents any medical staff who uses the endoscopic surgery system 1, such as a surgeon or an assistant of the surgery, and a scopist.

In the health care site, endoscopic surgeries have recently been carried out in the place of conventional abdominal surgeries. For example, in the case where an abdominal surgery is carried out, an endoscopic surgery system 1 which is arranged in a surgery room as shown in FIG. 1 is used. Instead of carrying out a laparotomy by cutting the abdominal wall as in the past, opening tools called trocars 12*a* and 12*b* are attached at several parts of the abdominal wall, and, through a hole provided to each of the trocars 12*a* and 12*b*, a laparoscope (hereinafter, may also be referred to as endoscope) 2, an energy treatment tool 3, a pair of forceps 4, and the like are inserted into the body. Then, while watching on a real-time basis an image of an affected part (tumor or the like) 16, which is captured as video by the endoscope 2 and displayed on a display device 9, procedures such as resecting the affected part 16 using the energy treatment tool 3 are performed. The endoscope 2, the energy treatment tool 3, and the pair of forceps 4 are held by a user, a robot, or the like. Note that, in the present embodiment, an example is described in which the endoscope 2 is a so-called rigid endoscope.

Inside the surgery room in which such an endoscopic surgery is carried out, there is provided a cart 14 which is loaded with devices for the endoscopic surgery, a patient's bed 13 on which a patient lies, a foot switch 15, and the like. The cart 14 is loaded with medical devices, such as a camera control unit (CCU) 5, a light source device 6, a treatment tool device 7, a pneumoperitoneum device 8, a display device 9, a recorder 10, and a printer 11.

An image signal of the affected part 16 which is acquired by imaging through an observation optical system of the endoscope 2 is transmitted to the CCU 5 via a camera cable, subjected to signal processing (image processing) in the CCU 5, and then output to the display device 9. Thus, an endoscope image of the affected part 16 is displayed. The CCU 5 may be connected to the endoscope 2 via the camera cable, or may be wirelessly connected to the endoscope 2. Note that, in the present description, the image acquired by capturing inside a living body may be referred to as "in-vivo image". Further, in the present description, an image acquired by imaging is referred to as "captured image", and the captured image may include an in-vivo image.

The light source device 6 is connected to the endoscope 2 via a light guide cable, and can irradiate the affected part 16 with light beams having various different wavelengths in a switching manner. The treatment tool device 7 is a high-frequency output device that outputs a high-frequency current to the energy treatment tool 3 which cuts the affected part 16 using electrical heat, for example. The pneumoperitoneum device 8 includes air-supply means and air-suction means, and is a device that supplies the inside of the body of a patient, for example, the abdominal region, with air. The foot switch 15 uses a foot operation of the user as a trigger signal and controls the CCU 5, the treatment tool device 7, and the like.

1-2. Background

Heretofore, the overall configuration of the endoscopic surgery system 1 according to the present embodiment has been described. Subsequently, the background of why the endoscopic surgery system 1 according to the present embodiment has been produced will be described.

In an endoscopic surgery, in order to observe places in which organs are convoluted, there is a case where a perspective mirror having a line-of-sight direction whose angle is different from the angle of the movement direction is used in addition to a direct vision mirror having a line-of-sight direction whose angle is the same as the angle of the movement direction. In such a case, the user carries out the surgery while changing the body tubes (the direct vision mirror and the perspective mirror).

In this manner, since various endoscopes having different line-of-sight directions are used for different purposes during the surgery, it may take time and effort to prepare (cleansing, sterilizing, etc.) all the body tubes to be used before the surgery, and it may take time and effort to exchange body tubes during the surgery. In order to save those efforts, there is an endoscope capable of changing the angle of the line-of-sight direction.

However, in the case where such an endoscope capable of changing the angle of the line-of-sight direction is used, there was a case where it is difficult to grasp an angle of a current line-of-sight direction from an image which is captured by the endoscope and displayed on a monitor. In the case where the angle of the line-of-sight direction is unclear, it becomes difficult to manipulate the endoscope, and there is a risk that the organs such as the abdominal wall may be wounded.

Here, as the endoscope written in Patent Literature 1, for example, there is considered the endoscope in which a sensor for detecting an angle of a line-of-sight direction is provided inside a body tube of the endoscope, and a method of detecting the angle of the line-of-sight direction by transmitting sensor information acquired by the sensor to the CCU.

However, in the case where the endoscope includes the sensor and the mechanism for transmitting the sensor information to the CCU as described above, the structure of the endoscope becomes complicated. For example, in the case where the sensor information is transmitted from the endoscope to the CCU, it is necessary to provide the endoscope with a mechanism that electrically connects the body tube including the sensor to a camera head of the endoscope connected to the CCU. However, in the case where the body tube includes the sensor, and the body tube includes the mechanism for the electrical connection, it becomes more difficult to perform cleansing and sterilizing (for example, sterilizing by heating) of the body tube.

Accordingly, the present embodiment has been made in view of the circumstances described above. The endoscopic surgery system 1 according to the present embodiment can decrease complications of the endoscope 2, and can enable the user to grasp the angle of the line-of-sight direction although the endoscope 2 does not have the mechanism that electrically connects the body tube to the camera head. Hereinafter, there will be given successively detailed description of the configurations of the endoscope 2 and the CCU 5 included in the endoscopic surgery system 1 according to the present embodiment for achieving those effects.

2. Configuration

2-1. Configuration of Endoscope

FIG. 2 is a block diagram showing an example of a functional configuration of an endoscope 2 according to an embodiment of the present disclosure. As shown in FIG. 2, the endoscope 2 according to the present embodiment includes a body tube 20 and a camera head 200. Further, the endoscope 2 according to the present embodiment is capable of changing an angle of a line-of-sight direction without exchanging body tubes 20.

As shown in FIG. 2, the body tube 20 includes an objective lens 22, an image formation optical system 24, and an angle adjustment unit 26. Note that, although only the objective lens 22 and the image formation optical system 24 are shown as the optical members included in the body tube 20 in FIG. 2, other optical members such as a cap or a filter that transmits light may also be present between the objective lens 22 and a subject or between the objective lens 22 and the image formation optical system 24.

The objective lens 22 is a lens (optical member or optical element) that transmits light from the subject. Note that the lens according to an embodiment of the present disclosure does not necessarily have a function of refracting light, and, in the present disclosure, an optical member that transmits at least some of the incident light is called a lens.

FIG. 3 is an explanatory diagram illustrating the objective lens 22. The objective lens 22 does not move or rotate with respect to a housing of the body tube 20, and the body tube 20 may be capable of changing the angle of the line-of-sight direction using the mechanism of the image formation optical system 24 and the angle adjustment unit 26 to be described later. As shown in FIG. 3, the objective lens 22 may transmit the light from the line-of-sight direction of 0° to 120°, for example.

Further, the objective lens 22 according to the present embodiment includes a marker. The marker may show the angle of the line-of-sight direction, for example. Hereinafter, examples of the objective lens 22 that has a marker will be described.

FIG. 4 is an explanatory diagram illustrating an example of the objective lens 22 (objective lens 22-1) having a marker. The objective lens 22-1 shown in FIG. 4 has a marker 221 (marker portions 221A to D) and a marker 223 (marker portions 223A to C) at the left and right ends of a light transmitting part 220-1. The marker 221 and the marker 223 includes multiple colors corresponding to angles of line-of-sight directions, respectively (hereinafter, may be referred to as color patterns). With such a structure, a user, or a CCU 5 to be described later can recognize the angle of the current line-of-sight direction on the basis of the regions corresponding to the marker 221 and the marker 223 included (shown) in the captured image.

Note that, in the example shown in FIG. 4, the marker portions 221A to D have different colors from each other, and the marker portions 223A to C also have different colors from each other. For example, the user, or the CCU 5 to be described later can recognize the angle of the current line-of-sight direction by recognizing which of the marker portions 221A to D and which of the marker portions 223A to C are included in the captured image.

Further, the marker 221 and the marker 223 may be translucent, and may transmit at least some of the incident light, for example. With such a structure, the captured image based on the light that has transmitted through the objective lens 22-1 may include information of the light that has transmitted through the marker 221 and the marker 223. Further, with the image processing performed by the CCU 5, an image which makes the user not conscious of the marker 221 and the marker 223 may also be displayed through image processing performed by the CCU 5 as will be described later.

Note that, in the case where the marker 221 and the marker 223 are translucent, it is desirable that the marker 221 and the marker 223 have different colors from the colors that an observation target (for example, inside a living body) or a surgery tool may have. With such a structure, it makes easier for the user to visually recognize the marker 221 and the marker 223, and further, the accuracy of recognizing the angle of the line-of-sight direction by the CCU 5 may be enhanced.

Further, the color patterns included in the marker 221 and the marker 223 may correspond to angles of hues, for example. With such a structure, in the case where the user has knowledge of the hues, for example, the user can grasp the angle of the current line-of-sight direction by visually recognizing the regions corresponding to the marker 221 and the marker 223 included in the captured image, without newly learning the correspondence between the color patterns and the angles.

Further, as shown in FIG. 4, between the marker 221 and the marker 223 at the left and right, positions of boundaries of color patterns in the vertical direction may differ. For example, in the example shown in FIG. 4, the position in the vertical direction of the boundary between the marker portion 221A and the marker portion 221B is different from the position in the vertical direction of the boundary between the marker portion 223A and the marker portion 223B. With such a structure, the combination of the marker 221 and the marker 223 can indicate a further detailed angle, and, for example, detection performance (resolution) of the angle of the CCU 5 can be enhanced.

Note that an example of a captured image in the case where the objective lens 22-1 shown in FIG. 4 is used will be described later with reference to FIG. 8.

FIG. 5 is an explanatory diagram illustrating another example of the objective lens 22 (objective lens 22-2) having a marker. The objective lens 22-2 shown in FIG. 5 has a marker 225 (marker portions 225A to C) at the center part in the horizontal direction of a light transmitting part 220-2. In the example shown in FIG. 5, the marker portion 225A, the marker portion 225B, and the marker portion 225C have different colors from each other, and have color patterns indicating different angles of the line-of-sight directions from each other.

With such a structure, even in the case where the endoscope 2 has an optical zoom function that enables changing of the focal distance, for example, the grasping of the angle of the line-of-sight direction may become easier, since the marker 225 arranged at the center part in the horizontal direction of the light transmitting part 220-2 may be included in the captured image.

Further, the marker 225 may also include color patterns corresponding to angles of hues in the same manner as the marker 221 and the marker 223 described with reference to FIG. 4. Further, the marker 225 may also be translucent in the same manner as the marker 221 and the marker 223 described with reference to FIG. 4.

Further, it is desirable that the marker portions 225A to C be arranged such that any one of the marker portions 225A to C is included in the captured image all the time even in the case where the line-of-sight direction is changed in any manner.

Note that FIG. 5 shows an example in which a marker is not present (is transparent) between the marker portion 225A and the marker portion 225B and between the marker portion 225B and the marker portion 225C, but the marker portions 225A to C may also be arranged continuously in the vertical direction. With such a structure, even in the case where the endoscope 2 has the optical zoom function, for example, a part of the marker 225 is included in the captured image all the time, and the angle can be grasped.

FIG. 6 is an explanatory diagram illustrating another example of the objective lens 22 (objective lens 22-3) having a marker. The objective lens 22-3 shown in FIG. 6 has a marker 227 including a scale mark indicating the angle of the line-of-sight direction and character strings (0°, 40°, 80°, and 120°) indicating the angles of the line-of-sight direction on a light transmitting part 220-3.

With such a structure, even in the case where the CCU 5 does not perform angle detection or image processing, the user can recognize the angle of the line-of-sight direction more easily than the case where the user observes the captured image based on the light that has transmitted through the objective lens 22-3. Note that, although FIG. 6 shows an example in which the marker 227 includes the scale mark indicating the angle of the line-of-sight direction and the character strings indicating the angles of the line-of-sight direction, the marker 227 may include only one of those.

Heretofore, description has been made on the objective lens 22. Note that the examples described above is merely an example, and the objective lens 22 according to the present embodiment is not limited to the examples shown in FIGS. 4 to 6. For example, the objective lens 22 according to the present embodiment may include the above-mentioned markers in combination.

Subsequently, returning to FIG. 2, the description on the configuration of the endoscope 2 will be continued. The image formation optical system 24 (i.e. optical formation device) shown in FIG. 2 is optically connected to the objective lens 22, and forms an image of the light transmitted through the objective lens 22. The image formation optical system 24 may include multiple lenses, for example, and, among the multiple lenses included in the image formation optical system 24, at least some of the lenses may be included on the inner side. Further, among the multiple lenses included in the image formation optical system 24, the image formation optical system 24 may be capable of changing the angle of the line-of-sight direction with at least some of the lenses being moved or being rotated. Further, the movement and the rotation of the lenses may be performed in conjunction with a user operation on the angle adjustment unit 26 to be described later.

Note that, since the configuration for changing the angle of the line-of-sight direction is known, the detailed description on the image formation optical system 24 will be omitted.

The angle adjustment unit 26 is used for the user to adjust the angle of the line-of-sight direction, and may include a dial, for example. For example, with the user rotating the dial, a lens included in the image formation optical system 24 moves or rotates in conjunction with the rotation, and thus, the angle of the line-of-sight direction can be adjusted.

The camera head 200 is optically connected to the body tube 20 as shown in FIG. 2 and includes an image sensor 202 (e.g. the image capturing device). The camera head 200 is not necessarily electrically connected to the body tube 20.

The image sensor 202 acquires a captured image by receiving, on a photosensitive surface of the image sensor 202, light transmitted through the objective lens 22 which is subjected to image formation by the image formation optical system 24. To be specific, the image sensor 202 includes the photosensitive surface having light receiving elements such as photodiodes arranged thereon, receives light on the photosensitive surface, and acquires a captured image through photoelectric conversion.

Examples of the image sensor 202 include known image sensors such as a charge coupled device (CCD) image sensor and a complementary metal-oxide-semiconductor (CMOS) image sensor. The captured image acquired by the image sensor 202 is transmitted to the CCU 5 to be described later.

2-2. Configuration of CCU

Heretofore, the configuration example of the endoscope 2 has been described. Subsequently, with reference to FIG. 7, a configuration example of a CCU 5-1, which is an example of the CCU 5 (e.g. processing circuitry) according to the present embodiment, will be described. FIG. 7 is a block diagram showing an example of a functional configuration of the CCU 5-1. As shown in FIG. 7, the CCU 5-1 according to the present embodiment is an image processing apparatus including an angle specification unit 52 and an image processing unit 54.

The angle specification unit 52 specifies (detects) the angle of the line-of-sight direction on the basis of the captured image transmitted from the camera head 200 described with reference to FIG. 2. As described above, the captured image is acquired (captured) on the basis of the light transmitted through the objective lens 22, and the angle specification unit 52 may perform image recognition processing corresponding to the marker on the objective lens 22 and may specify the angle of the line-of-sight direction.

For example, in the case where the objective lens 22-1 shown in FIG. 4 is used, the angle specification unit 52 may specify the angle of the line-of-sight direction on the basis of color information of a region corresponding to the marker 221 and the marker 223 included in the captured image. Further, in such a case, the angle specification unit 52 may specify positions corresponding to boundaries of color patterns in the marker 221 and the marker 223 on the captured image, and may specify the angle of the line-of-sight direction on the basis of the positions.

Further, in the case where the objective lens 22-2 shown in FIG. 5 is used, the angle specification unit 52 may detect a region corresponding to any one of the marker portions 255A to C at the center part in the horizontal direction of the captured image, and may analyze color information of the region, to thereby specify the angle of the line-of-sight direction.

Further, in the case where the objective lens 22-3 shown in FIG. 6 is used, the angle specification unit 52 may specify the angle of the line-of-sight direction by recognizing the scale mark or the number indicating the angle of the line-of-sight direction included in the region corresponding to the marker 227 included in the captured image.

The angle specification unit 52 provides the image processing unit 54 with the angle of the line-of-sight direction that has been specified.

The image processing unit 54 performs image processing on the captured image transmitted from the camera head 200 on the basis of the angle of the line-of-sight direction specified by the angle specification unit 52, and generates an output image. For example, the image processing unit 54 may have functions as a color correction unit 542 and a combining unit 544 as shown in FIG. 7.

The color correction unit 542 performs color correction processing (an example of image processing) involving subtracting a color included in a marker of the objective lens 22 on the basis of the angle of the line-of-sight direction. The color correction unit 542 may perform color correction processing corresponding to the marker of the objective lens 22.

For example, in the case where the objective lens 22-1 shown in FIG. 4 is used, the color correction unit 542 may perform color correction processing involving subtracting a color corresponding to the angle of the line-of-sight direction on the regions corresponding to the marker 221 and the marker 223 included in the captured image.

Further, in the case where the objective lens 22-2 shown in FIG. 5 is used, the color correction unit 542 may perform color correction processing involving subtracting a color corresponding to the angle of the line-of-sight direction (color corresponding to the detected marker) on a region corresponding to any one of the marker portions 255A to C detected from the captured image.

The combining unit 544 performs combining processing (an example of image processing) involving combining an indicator indicating the angle of the line-of-sight direction with the image which has been subjected to the color correction processing by the color correction unit 542. For example, the indicator that the combining unit 544 combines may include a character string indicating the angle of the line-of-sight direction.

Note that the image processing unit 54 may also perform image processing such as gamma-correction processing or white balance adjustment processing, in addition to the above-mentioned image processing.

The output image that is generated by being subjected to the image processing by the image processing unit 54 is output to the display device 9 described with reference to FIG. 1, and is displayed on the display device 9.

FIG. 8 is an explanatory diagram showing an example of a captured image and an output image. FIG. 8 shows an example of a captured image G10 and an output image G20 in the case where the objective lens 22-1 shown in FIG. 4 is used.

The captured image G10 shown in FIG. 8 includes a region G12 corresponding to the marker 221, and a region G14 corresponding to the marker 223. Further, the region G12 is obtained on the basis of the light transmitted through the translucent marker portion 221C, and the region G14 is obtained on the basis of the light transmitted through the translucent marker portion 223B and the translucent marker portion 223C.

The angle specification unit 52 to which the captured image G10 shown in FIG. 8 is input specifies the angle of the line-of-sight direction on the basis of color information of the region G12 and the region G14, and of positions corresponding to the boundaries of the color patterns included in the regions.

The output image G20 shown in FIG. 8 is generated by subjecting the captured image G10 to the image processing performed by the image processing unit 54, and is an output image displayed on the display device 9. As shown in FIG. 8, a user observing the output image G20 is capable of performing observation without being influenced by the marker 221 and the marker 223 through color correction processing involving subtracting colors in the region G22 corresponding to the marker 221 and the region G24 corresponding to the marker 223.

Further, the output image G20 shown in FIG. 8 includes an indicator G26 indicating the angle of the line-of-sight direction. With the indicator G26, the user observing the output image G20 is capable of easily grasping the angle of the line-of-sight direction.

Heretofore, the configuration example according to the present embodiment has been described. Note that the above-mentioned configuration example is merely an example, and the present embodiment is not limited to such an example. For example, the CCU 5 does not necessarily have functions of the color correction unit 542 and the combining unit 544, and does not necessarily perform the correction processing involving subtracting a color or the combining processing on the captured image. In such a case, the user may grasp the angle of the line-of-sight direction from the marker shown on the displayed image. In particular, in the case where the objective lens 22-3 described with reference to FIG. 6 is used, the user can easily grasp the angle of the line-of-sight direction even in the case where the indicator indicating the angle of the line-of-sight direction is not combined with the displayed image.

3. Operation

Heretofore, the configuration example of the present embodiment has been described. Subsequently, an operation example according to the present embodiment will be described with reference to FIG. 9. FIG. 9 is a flowchart showing an operation example of the present embodiment. Note that, among the operations according to the present embodiment, FIG. 9 mainly shows processing performed by the CCU 5-1.

First, as shown in FIG. 9, the angle specification unit 52 specifies an angle of a line-of-sight direction on the basis of a captured image (S102).

Subsequently, the color correction unit 542 of the image processing unit 54 performs color correction processing involving subtracting a color corresponding to the marker of the objective lens 22 on the captured image (S104).

Subsequently, the combining unit 544 of the image processing unit 54 performs combining processing involving combining a character string (an example of an indicator) indicating an angle with the image that has been subjected to the color correction processing of Step S104 (S106).

An output image obtained by the image processing (color correction processing and combining processing) performed by the image processing unit 54 is output to the display device 9, and is displayed on the display device 9 (S108).

The series of processing (S102 to S108) described above may be repeated as appropriate.

4. Modified Examples

Heretofore, an embodiment of the present disclosure has been described. Hereinafter, several modified examples of an embodiment of the present disclosure will be described. Note that each of the modified examples described below may be applied to the embodiment of the present disclosure individually, or may be applied to the embodiment of the present disclosure in combination. Further, each of the modified examples may be applied in the place of the configuration described in the embodiment of the present disclosure, or may be applied additionally to the configuration described in the embodiment of the present disclosure.

4-1. Modified Example 1

(Overview)

In the above embodiment, the example in which the image processing is performed on the basis of the angle of the line-of-sight direction specified by the angle specification unit 52 has been described, but the present technology is not limited to such an example. For example, the angle of the line-of-sight direction specified by the angle specification unit 52 may also be used for processing other than the image processing. Hereinafter, as Modified Example 1, an example in which the angle of the line-of-sight direction specified by the angle specification unit 52 is used for control on a light source (illumination) will be described.

FIG. 10 is an explanatory diagram illustrating an overview of the present modified example. As shown in FIG. 10, a body tube 20-2 according to the present modified example includes light output units 27 (light output units 27A to 27F) that output illumination light to an outside along the objective lens 22. For example, the light output from the light source device 6 described with reference to FIG. 1 may be introduced to the body tube 20-2 through a light cable (not shown), and may be output from the light output units 27 to the outside.

Here, if the light is output from all the light output units 27A to 27F, light that does not contribute to imaging may be output, and there is a risk that increase in power consumption and decrease in light source life may be caused. Accordingly, the description will be made below on a mechanism for reducing the power consumption and suppressing the decrease in the light source life by, performing control on the light source on the basis of the angle of the line-of-sight direction.

(Configuration)

First, hereinafter, with reference to FIG. 11, a configuration example of a CCU 5-2, which is an example of the CCU 5 according to the present modified example, will be described. FIG. 11 is a block diagram showing an example of a functional configuration of the CCU 5-2. As shown in FIG. 7, the CCU 5-2 according to the present modified example is an image processing apparatus including an angle specification unit 52, an image processing unit 54, and a light source controller 56. The configuration of the angle specification unit 52 and the configuration of the image processing unit 54 shown in FIG. 11 are substantially the same as the configuration of the angle specification unit 52 and the configuration of the image processing unit 54 described with reference to FIG. 7, respectively, and hence, the description thereof will be omitted here.

The light source controller 56 controls a light source on the basis of the angle of the line-of-sight direction specified by the angle specification unit 52. For example, the light source controller 56 may control the light source by outputting a control signal for controlling the light source to the light source device 6 described with reference to FIG. 1.

The light source controller 56 may control the light source such that, among the multiple light output units 27 (light output units 27A to 27F), light is output from one or multiple light output units that contribute to imaging and light is not output from the other light output unit(s) that does(/do) not contribute to imaging, the output units being specified in accordance with the angle of the line-of-sight direction, for example. For example, in the case where the light source device 6 includes multiple light sources, and the light sources correspond to the light output units 27A to 27F, the control may be performed such that the light source(s) corresponding to the light output unit(s) 27 that contributes (/contribute) to imaging is(/are) turned on, and the other light source(s) is(/are) turned off. Note that the light source controller 56 not only performs the complete on/off control, but may also control the light sources such that, a stronger voltage is applied to the light source(s) that contributes(/ contribute) more to imaging and a weaker voltage is applied to the light source(s) that does(/do) not contribute to imaging.

(Operation)

Heretofore, the configuration example of the present modified example has been described. Subsequently, an operation example of the present modified example will be described with reference to FIG. 12. FIG. 12 is a flowchart showing an operation example of the present modified example. Note that, among the processing shown in FIG. 12, the processing of Steps S202 to S208 is similar to the processing of Steps S102 to S108 described with reference to FIG. 9, and hence, the description of the processing of Steps S202 to S208 will be omitted.

As shown in FIG. 12, after Step S208, the light source controller 56 specifies, among the light output units 27, a light output unit corresponding to the angle of the line-of-sight direction specified in Step S202 (S210). In addition, the light source controller 56 outputs a light source control signal to the light source device 6 (S212).

(Supplement)

Heretofore, the configuration example and the operation example of Modified Example 1 have been described. According to Modified Example 1 described above, the power consumption can be reduced and the decrease in the light source life can be suppressed by performing control on the light source on the basis of the angle of the line-of-sight direction.

Note that, in the example described above, an example in which the light source device 6 has the light source and the light source controller 56 outputs a control signal for controlling the light source to the light source device 6 has been described, but the present modified example is not limited to such an example. For example, in the case where an endoscope or a body tube has a light source, the light source controller 56 may output a control signal for controlling the light source to the endoscope or the body tube.

4-2. Modified Example 2

(Overview)

In the above embodiment, the example in which the color correction processing and the combining processing are performed on the basis of the angle of the line-of-sight direction specified by the angle specification unit 52 has been described, but the present technology is not limited to such an example. For example, image processing other than the color correction processing and the combining processing may be performed on the basis of the angle of the line-of-sight direction specified by the angle specification unit 52. Hereinafter, as Modified Example 2, an example in which camera shake correction processing is performed on the basis of the angle of the line-of-sight direction specified by the angle specification unit 52 will be described.

As has been described with reference to FIG. 2, the endoscope 2 is capable of changing the angle of the line-of-sight direction through a manipulation such as rotating the angle adjustment unit 26 at hand. With such a manipulation, there is a risk that camera shake may occur, and the camera shake may be a factor for inhibiting a surgical technique of a user observing an image based on the imaging performed by the endoscope 2. In the case where such camera shake has occurred, it is assumed that camera shake correction processing is performed, which is processing for reducing disturbance of an image caused by the camera shake. However, if known camera shake correction processing is performed, there is a risk that the movement of the image caused by the change (rotation) of the angle of the line-of-sight direction itself may also be suppressed, and there is a risk that the user is provided with the image that is unnatural to the user. Accordingly, the description will be made below on a mechanism for performing the camera shake correction processing more naturally by performing the camera shake correction processing on the basis of the angle of the line-of-sight direction.

(Configuration)

First, hereinafter, with reference to FIG. 13, a configuration example of a CCU 5-3, which is an example of the CCU 5 according to the present modified example, will be described. FIG. 13 is a block diagram showing an example of a functional configuration of the CCU 5-3. As shown in FIG. 13, the CCU 5-3 according to the present modified example is an image processing apparatus including an angle specification unit 52, a rotation direction specification unit 53, and an image processing unit 55. The configuration of the angle specification unit 52 shown in FIG. 13 is substantially the same as the configuration of the angle specification unit 52 described with reference to FIG. 7, and hence, the description thereof will be omitted here.

The rotation direction specification unit 53 specifies a rotation direction of the line-of-sight direction (direction in which the line-of-sight direction changes in conjunction with a user operation on the angle adjustment unit 26) on the basis of the angle of the line-of-sight direction specified by the angle specification unit 52. For example, the rotation direction specification unit 53 specifies the rotation direction of the line-of-sight direction on the basis of the time-series change of the angle of the line-of-sight direction. The rotation direction specification unit 53 provides the image processing unit 55 with the specified rotation direction.

The image processing unit 55 performs the camera shake correction processing on the captured image, on the basis of the rotation direction of the line-of-sight direction that has been specified on the basis of the angle of the line-of-sight direction. For example, the image processing unit 55 according to the present modified example has functions as a motion detector 551, a motion correction unit 553, an affine coefficient calculation unit 555, and an affine transformation unit 557. The image processing unit 55 outputs an output image obtained by performing image processing for camera shake correction on the captured image to the display device 9.

The motion detector 551 acquires motion information indicating motion from a time-series captured image transmitted from the camera head 200. The motion information may be a motion vector (MV), for example.

The motion correction unit 553 performs motion correction processing for suppressing a component corresponding to the rotation direction specified by the rotation direction specification unit 53, with respect to the motion information. For example, the motion correction unit 553 may perform processing such that, among the motion information, the component corresponding to the rotation direction is set to 0. The motion correction unit 553 provides the affine coefficient calculation unit 555 with the corrected motion information obtained by the motion correction processing.

The affine coefficient calculation unit 555 calculates an affine coefficient for the camera shake correction on the basis of the corrected motion information obtained by the motion correction unit 553.

The affine transformation unit 557 performs affine transformation processing on the captured image using the affine coefficient calculated by the affine coefficient calculation unit 555.

(Operation)

Heretofore, the configuration example of the present modified example has been described. Subsequently, an operation example of the present modified example will be described with reference to FIG. 14. FIG. 14 is a flowchart showing an operation example of the present modified example.

First, as shown in FIG. 14, the angle specification unit 52 specifies an angle of a line-of-sight direction on the basis of a captured image (S302). Subsequently, the rotation direction specification unit 53 specifies a rotation direction on the basis of a time-series change of the angle specified in Step S302 (S304).

Subsequently, the motion detector 551 of the image processing unit 55 acquires motion information indicating a motion from the captured image (S306). In addition, the motion correction unit 553 of the image processing unit 55 performs motion correction processing for suppressing, among the motion information, a component corresponding to the rotation direction specified in Step S306 (S308).

Subsequently, the affine coefficient calculation unit 555 of the image processing unit 55 calculates an affine coefficient for the camera shake correction on the basis of the corrected motion information obtained by the motion correction processing of Step S308 (S310). In addition, the affine transformation unit 557 of the image processing unit 55 performs affine transformation processing on the captured image using the affine coefficient calculated in Step S310 (S312).

The output image obtained by the affine transformation processing is output to the display device 9, and is displayed on the display device 9 (S314).

(Supplement)

Heretofore, the configuration example and the operation example of Modified Example 2 have been described. According to Modified Example 2, the camera shake correction processing can be performed more naturally by performing the camera shake correction processing on the basis of the angle of the line-of-sight direction.

Note that the camera shake correction processing through the above-mentioned affine transformation is merely an example, and the present modified example is not limited to such an example and can be applied to various types of camera shake correction processing.

Further, although an example in which the motion correction processing is performed on the basis of the rotation direction has been described above, the motion correction processing may be performed also on the basis of a rotation amount. For example, in the case where a distance to a subject can be acquired, the rotation amount of a line-of-sight direction can be specified on the basis of the angle of the line-of-sight direction. For example, the motion of the image caused by the rotation of the line-of-sight direction can be excluded from the motion information more accurately by performing motion correction on the basis of the rotation direction and the rotation amount. Further, in addition to the above-mentioned functions, the image processing unit 55 may also have functions as the color correction unit 542 and the combining unit 544 in the similar manner as the image processing unit 54 described with reference to FIG. 7.

4-3. Modified Example 3

In the above embodiment, an example in which the objective lens 22 included in the body tube 20 has the marker, but the present technology is not limited to such an example. For example, an optical member (such as a cap or a filter that transmits at least some light) that is attachable to and detachable from the body tube 20 may have a marker. In such a case, the light transmitted through the optical member may enter the objective lens 22. Further, the optical member may be optically connected to the image formation optical system 24 via the objective lens 22. Note that, in such a case, the objective lens 22 does not necessarily have a marker.

5. Hardware Configuration Example

Heretofore, the embodiment and the modified examples of the present disclosure have been described. The pieces of information processing such as the angle specification processing, the image processing, and the light source control processing described above are achieved by cooperation of software, and hardware of the CCU 5 (CCU 5-1, CCU 5-2, and CCU 5-3) to be described below, for example.

FIG. 15 is an explanatory diagram showing an example of a hardware configuration of the CCU 5. The CCU 5 includes, for example, an FPGA board 501, a CPU 502, GPU boards 5031 and 5032, a memory 504, an IO controller 505, a recording medium 506, and an interface 507. Further, the FPGA board 501, the CPU 502, and the GPU boards 5031 and 5032 are connected to each other via a bus 508, for example. The FPGA board 501 includes, for example, an FPGA, an input interface through which an input image signal (captured image signal) is input from an AV controller 110 or the endoscope 2, and an output interface through which an output image signal is output to the AV controller 110 or the display device 9.

The CPU 502, and the GPU boards 5031 and 5032 execute various types of software such as related software, and performs various types of processing. The CPU 502 includes a processor. The GPU boards 5031 and 5032 each include a graphics processing unit (GPU) and a dynamic random access memory (DRAM).

The memory 504 stores various types of data such as data corresponding to the input image signal and data corresponding to the output image signal. The CPU 502 has a role of controlling writing of various types of data in the memory 504 and reading of various types of data from the memory 504.

The CPU 502 divides image data stored in the memory 504 in accordance with data stored in the memory 504, processing capacity of the GPU boards 5031 and 5032, and processing details. Then, the GPU's of the respective GPU boards 5031 and 5032 perform predetermined processing on supplied divided data and output the processing results to the CPU 502.

The IO controller 505 has a role of controlling transmission of signals between the CPU 502, the recording medium 506, and the interface 507, for example.

The recording medium 506 functions as a storage (not shown), and stores various types of data such as image data and applications. Here, there is given a solid-state drive as an example of the recording medium 506. Further, the recording medium 506 may be attachable to and detachable from the CCU 5.

Examples of the interface 507 include a universal serial bus (USB) terminal and a processing circuit, and a local area network (LAN) terminal and a transmission/reception circuit.

Note that the hardware configuration of the CCU 5 is not limited to the configuration shown in FIG. 15. For example, although FIG. 15 shows an example in which two GPU boards 5031 and 5032 are included, the number of GPU boards may be more than two. Further, in the case where the CPU 502 has a function of a GPU, the CCU 5 does not necessarily include the GPU boards 5031 and 5032.

Note that a computer program for achieving each function of the CCU 5 according to the above present embodiment can be created. Further, a computer-readable recording medium that stores the computer program can be provided as well. Examples of the recording medium include a magnetic disk, an optical disc, a magneto-optical disk, and a flash memory. The computer program may be delivered via a network for example, without using the recording medium. Moreover, the number of computers for executing the computer program is not particularly limited. For example, the computer program may be executed by multiple computers (for example, multiple servers) in cooperation with each other.

6. Conclusion

As described above, according to the embodiment of the present disclosure, the angle of the line-of-sight direction can be grasped more easily.

It should be understood by those skilled in the art that various modifications, combinations, sub-combinations and alterations may occur depending on design requirements and other factors insofar as they are within the scope of the appended claims or the equivalents thereof.

For example, the steps in the above embodiment may not necessarily be executed in a time-series manner in the order described in the flowcharts. The steps in the processes in the above embodiment may also be executed in, for example, a different order from the order described in the flowcharts, or may be executed in parallel.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An endoscopic system including:
an endoscope including
an optical element including a marker disposed thereon,
an optical formation device configured to change an angle of view, and
an image capturing device receiving light from the optical element via the optical formation device; and
processing circuitry configured to
identify the angle of view from an image captured by the image capturing device based on the marker in the image.

(2)
The endoscopic system according to (1), wherein the processing circuitry is further configured to control display of the identified angle of view on a display.

(3)
The endoscopic system according to (1)-(2), wherein the processing circuitry is further configured to control display of the identified angle of view on the display as a number.

(4)
The endoscopic system according to (1)-(3), wherein the processing circuitry is further configured to control display of the image captured by the image capturing device without displaying the marker in the image by processing the image.

(5)
The endoscopic system according to (1)-(4), wherein the endoscope further includes a light source and the processing circuitry is further configured to control a direction of the light source.

(6)
The endoscopic system according to (5), wherein the processing circuitry is further configured to control the light source based on the identified angle of view.

(7)
The endoscope system according to (1)-(6), wherein the marker includes a plurality of colors.

(8)
The endoscope system according to (1)-(7), wherein the marker is positioned on two sides of the objective lens.

(9)
The endoscope system according to (1)-(8), wherein the marker is positioned on two sides of the objective lens and different color patterns are included on each side.

(10)
The endoscope system according to (1)-(9), wherein the processing circuitry is further configured to process the image based on the identified angle of view.

(11)
The endoscope system according to (10), wherein the processing circuitry is further configured to process the image with camera shake correction processing based on the identified angle of view.

(12)
The endoscope system according to (10), wherein the optical element is an objective lens.

(13)
The endoscope system according to (12), wherein the objective lens is movable independent of the endoscope.

(14)
A medical image processing device, including:
processing circuitry configured to
identify an angle of view from an image based on a marker in the image,
wherein the image is generated from light through the marker on an optical element, and
wherein the angle of view is changed relative to the marker in an endoscope imaging device.

(15)
The medical image processing device according to (14), wherein the processing circuitry is further configured to control display of the identified angle of view on a display.

(16)
The medical image processing device according to (14)-(15), wherein the processing circuitry is further configured to control display of the identified angle of view on the display as a number.

(17)
The medical image processing device according to (14)-(16), wherein the processing circuitry is further configured to control display of the image captured by the image capturing device without displaying the marker in the image by processing the image.

(18)
The medical image processing device according to (14)-(17), wherein the endoscope further includes a light source and the processing circuitry is further configured to control a direction of the light source.

(19)
The medical image processing device according to (18), wherein the processing circuitry is further configured to control the light source based on the identified angle of view.

(20)
The medical image processing device according to (14)-(19), wherein the processing circuitry is further configured to process the image based on the identified angle of view.

(21)
The medical image processing device according to (20), wherein the processing circuitry is further configured to process the image with camera shake correction processing based on the identified angle of view.

(22)
A medical image processing method, including:
identifying, via processing circuitry, an angle of view from an image based on a marker in the image,
wherein the image is generated from light through the marker on an optical element, and
wherein the angle of view is changed relative to the marker in an endoscope imaging device including the marker and the optical element.

(23)
An endoscope comprising:
an optical element including a marker disposed thereon; and
an optical formation device configured to change an angle of view relative to the marker on the optical element.

(24)
The endoscope according to (23), further comprising:
an image capturing device receiving the light passing through the marker on the optical element.

(25)
An image processing apparatus including:
an angle specification unit configured to specify an angle of a line-of-sight direction on the basis of an in-vivo image based on light transmitted through an optical member, the optical member including a marker and being optically connected to an image formation optical system capable of changing the angle of the line-of-sight direction; and
an image processing unit configured to perform image processing on the in-vivo image.

(26)
An image processing apparatus according to (25), in which
the image processing unit performs image processing based on the angle specified by the angle specification unit.

(27)
The image processing apparatus according to (26), in which the marker includes a plurality of colors corresponding to the angle, and the angle specification unit specifies the angle on the basis of color information of a region corresponding to the marker included in the in-vivo image.

(28)
The image processing apparatus according to (27), in which
the optical member includes a plurality of markers,
in the plurality of markers, positions of boundaries of the plurality of colors in a vertical direction are different for each of the markers, and
the angle specification unit specifies the angle further on the basis of positions corresponding to the boundaries in the in-vivo image.

(29)
The image processing apparatus according to (27) or (28), in which
the marker is translucent, and
the image processing unit performs image processing involving subtracting a color corresponding to the angle on a region corresponding to the marker included in the in-vivo image.

(30)
The image processing apparatus according to any one of (26) to (29), in which
the image processing unit performs image processing involving combining an indicator indicating the angle.

(31)
The image processing apparatus according to any one of (25) to (30), in which
the image processing unit performs camera shake correction processing based on the angle specified by the angle specification unit.

(32)
The image processing apparatus according to (31), in which
the image processing unit performs the camera shake correction processing on the basis of, among motion information acquired from the in-vivo image, corrected motion information acquired by suppressing a component corresponding to a rotation direction specified on the basis of the angle.

(33)
The image processing apparatus according to any one of (25) to (32), further including a light source controller configured to perform light source control based on the angle specified by the angle specification unit.

(34)
The image processing apparatus according to (33), in which
the light source controller performs light source control in a manner that a light source which is specified on the basis of the angle and which contributes to imaging is turned on and another light source is turned off.

(35)
The image processing apparatus according to (33), in which
the light source controller performs light source control in a manner that a light source that contributes more to imaging is provided with stronger power, on the basis of the angle.

(36)
The image processing apparatus according to any one of (25) to (35), in which the image formation optical system is included in an endoscope.

(37)
An image processing method including:
specifying, by a processor, an angle of a line-of-sight direction on the basis of an in-vivo image based on light transmitted through an optical member, the optical member including a marker and being optically connected to an image formation optical system capable of changing the angle of the line-of-sight direction; and performing image processing on the in-vivo image.

(38)
An optical member including
a marker, in which
the optical member is optically connected to an image formation optical system capable of changing an angle of a line-of-sight direction.

(39)
The optical member according to (38), in which
the marker includes a plurality of colors corresponding to the angle of the line-of-sight direction.

(40)
The optical member according to (39), in which
the optical member includes a plurality of markers, and
in the plurality of markers, positions of boundaries of the plurality of colors in a vertical direction are different for each of the markers.

(41)
The optical member according to (39) or (40), in which
the marker is located at a center part in a horizontal direction of the optical member.

(42)
The optical member according to any one of (39 to (41), in which
the marker is translucent.

(43)
The optical member according to (38), in which
the marker includes a scale mark indicating the angle of the line-of-sight direction or a character string indicating the angle of the line-of-sight direction.

REFERENCE SIGNS LIST 1 endoscopic surgery system
2 endoscope 3 energy treatment tool
4 forceps
5 CCU (camera control unit)
6 light source device
7 treatment tool device
8 pneumoperitoneum device
9 display device
10 recorder
11 printer
20 body tube
22 objective lens
24 image formation optical system
26 angle adjustment unit
27 light output unit
52 angle specification unit
53 rotation direction specification unit
54, 55 image processing unit
56 light source controller

The invention claimed is:

1. An endoscopic system comprising:
   an endoscope including
      an optical element including a marker disposed thereon, the optical element having a sector shape with thickness, and the maker being disposed on an arc area of the sector shape,
      an optical formation device configured to change an angle of view, and
      an image capturing device receiving light from the optical element via the optical formation device; and
   processing circuitry configured to
      identify the angle of view from an image captured by the image capturing device based on the marker in the image.

2. The endoscopic system according to claim 1, wherein the processing circuitry is further configured to control display of the identified angle of view on a display.

3. The endoscopic system according to claim 2, wherein the processing circuitry is further configured to control display of the identified angle of view on the display as a number.

4. The endoscopic system according to claim 1, wherein the processing circuitry is further configured to control display of the image captured by the image capturing device without displaying the marker in the image by processing the image.

5. The endoscopic system according to claim 1, wherein the endoscope further includes a light source and the processing circuitry is further configured to control a direction of the light source.

6. The endoscopic system according to claim 5, wherein the processing circuitry is further configured to control the light source based on the identified angle of view.

7. The endoscope system according to claim 1, wherein the marker includes a plurality of colors.

8. The endoscope system according to claim 1, wherein the marker is positioned on two sides of the arc area of the optical element.

9. The endoscope system according to claim 1, wherein the marker is positioned on two sides of the arc area of the optical element, and different color patterns are included on each side.

10. The endoscope system according to claim 1, wherein the processing circuitry is further configured to process the image based on the identified angle of view.

11. The endoscope system according to claim 10, wherein the processing circuitry is further configured to process the image with camera shake correction processing based on the identified angle of view.

12. The endoscope system according to claim 10, wherein the optical element is an objective lens.

13. The endoscope system according to claim 12, wherein the objective lens is movable independent of the endoscope.

14. The endoscopic system according to claim 1, wherein the optical formation device is configured to change the angle of view within a central angle of the sector shape of the optical element.

15. The endoscopic system according to claim 1, wherein the central angle of the sector shape of the optical element is greater than 0 degree and less than or equal to 120 degrees.

16. The endoscopic system according to claim 1, wherein
   the endoscope includes a body tube including the optical element and the optical formation device,
   the optical element is an objective lens, and
   the objective lens is disposed at a tip of the body tube.

17. A medical image processing device, comprising:
   processing circuitry configured to
      identify an angle of view from an image based on a marker in the image,
   wherein the image is generated from light through the marker on an optical element, the optical element having a sector shape with thickness, and the maker being disposed on an arc area of the sector shape, and
   wherein the angle of view is changed relative to the marker in an endoscope imaging device.

18. The medical image processing device according to claim 17, wherein the processing circuitry is further configured to control display of the identified angle of view on a display.

19. The medical image processing device according to claim 18, wherein the processing circuitry is further configured to control display of the identified angle of view on the display as a number.

20. The medical image processing device according to claim 17, wherein the processing circuitry is further configured to control display of the image captured by the image capturing device without displaying the marker in the image by processing the image.

21. The medical image processing device according to claim 17, wherein the endoscope imaging device further includes a light source and the processing circuitry is further configured to control a direction of the light source.

22. The medical image processing device according to claim 21, wherein the processing circuitry is further configured to control the light source based on the identified angle of view.

23. The medical image processing device according to claim 17, wherein the processing circuitry is further configured to process the image based on the identified angle of view.

24. The medical image processing device according to claim 23, wherein the processing circuitry is further configured to process the image with camera shake correction processing based on the identified angle of view.

25. A medical image processing method, comprising:
   identifying, via processing circuitry, an angle of view from an image based on a marker in the image,
   wherein the image is generated from light through the marker on an optical element, the optical element having a sector shape with thickness, and the maker being disposed on an arc area of the sector shape, and wherein the angle of view is changed relative to the marker in an endoscope imaging device including the marker and the optical element.

26. An endoscope comprising:
an optical element including a marker disposed thereon the optical element having a sector shape with thickness, and the maker being disposed on an arc area of the sector shape; and
an optical formation device configured to change an angle of view relative to the marker on the optical element.

27. The endoscope according to claim 26, further comprising:
an image capturing device receiving light passing through the marker on the optical element.

* * * * *